(12) United States Patent
Dworecki et al.

(10) Patent No.: US 10,429,346 B2
(45) Date of Patent: Oct. 1, 2019

(54) KIT FOR USE IN ELECTROPHORETIC MATRIX STAINING

(71) Applicant: Pierce Biotechnology, Inc., Rockford, IL (US)

(72) Inventors: Boguslawa R. Dworecki, Rockford, IL (US); Surbhi Desai, Rockford, IL (US); Gregory John Kilmer, Winnebago, IL (US); Peter Alan Bell, South Beloit, IL (US); Brian Lynn Webb, Roscoe, IL (US)

(73) Assignee: PIERCE BIOTECHNOLOGY, INC., Rockford, IL (US)

( * ) Notice: Subject to any disclaimer, the term of this patent is extended or adjusted under 35 U.S.C. 154(b) by 200 days.

(21) Appl. No.: 15/625,221

(22) Filed: Jun. 16, 2017

(65) Prior Publication Data

US 2017/0292932 A1 Oct. 12, 2017

Related U.S. Application Data

(62) Division of application No. 14/494,754, filed on Sep. 24, 2014, now Pat. No. 9,709,527.

(Continued)

(51) Int. Cl.
*G01N 27/447* (2006.01)
*G01N 1/30* (2006.01)

(52) U.S. Cl.
CPC ......... *G01N 27/44726* (2013.01); *G01N 1/30* (2013.01); *G01N 27/44739* (2013.01); *G01N 2001/302* (2013.01)

(58) Field of Classification Search
CPC ............... G01N 27/44726; G01N 1/30; G01N 27/44739; G01N 2001/302;
(Continued)

(56) References Cited

U.S. PATENT DOCUMENTS

| 4,021,324 A | 5/1977 | Delony et al. |
| 6,664,047 B1 | 12/2003 | Haughland et al. |

(Continued)

FOREIGN PATENT DOCUMENTS

| CN | 101936837 | 9/2012 |
| CN | 101936837 B | 9/2012 |
| WO | 2009/076312 | 6/2009 |

OTHER PUBLICATIONS

GenScript eStain® 2.0 Protein Staining System, available at www.genscript.com/estain_protein_straining_system.html (2002-2014).

(Continued)

*Primary Examiner* — Xiuyu Tai
(74) *Attorney, Agent, or Firm* — Baker Hostetler

(57) ABSTRACT

Staining compositions and methods for use with a matrix, such as an electrophoretic gel, containing separated biopolymers. The compositions including an acid, an organic solvent, and a generally planar, fluid-permeable gel contact sheet consisting primarily of a non-cellulosic material. The acid and organic solvent may be sorbed to the fluid-permeable gel contact sheet, or may be sorbed to a layers contactable with a non-gel contact side of the gel contact sheet. In one embodiment, the composition is a source electrophoretic stain composition including a staining reagent. In one embodiment, the composition is a sink electrophoretic stain composition including a sorbent.

20 Claims, 6 Drawing Sheets
(5 of 6 Drawing Sheet(s) Filed in Color)

Related U.S. Application Data

(60) Provisional application No. 61/882,951, filed on Sep. 26, 2013.

(58) Field of Classification Search
CPC ....... G01N 27/44747; G01N 33/54393; G01N 33/54306; G01N 7/44756; G01N 27/44
See application file for complete search history.

(56) References Cited

U.S. PATENT DOCUMENTS

| | | |
|---|---|---|
| 2006/0275917 A1 | 12/2006 | Wada |
| 2010/0044229 A1 | 2/2010 | Margalit et al. |
| 2010/0326828 A1 | 12/2010 | Wang et al. |
| 2014/0027284 A1 | 1/2014 | McKee |

OTHER PUBLICATIONS

Written Opinion of the International Searching Authority, PCT/US2014/057097, dated Dec. 10, 2014 (8 pages).
International Search Report PCT/US2014/057097 dated Dec. 10, 2014 (4 pages).
Notice of Transmittal of Written Opinion, International Search Report dated Dec. 10, 2014 (1 page).
International Preliminary Report on Patentability, PCT/US2014/057097, dated Apr. 7, 2016 (12 pages).

KIT FOR USE IN ELECTROPHORETIC MATRIX STAINING

This application is a division of co-pending U.S. patent application Ser. No. 14/494,754 filed Sep. 24, 2014, which claims the benefit of provisional U.S. Patent Application Ser. No. 61/882,951 filed Sep. 26, 2013, which are expressly incorporated by reference in their entirety.

Compositions, also referred to as consumables, and method for staining biopolymers such as proteins, nucleic acids, oligosaccharides, etc. in a matrix using an electric field. The staining composition has fluid-permeable sheet(s) that is/are brought into contact with the matrix. In one embodiment the fluid-permeable sheet(s) is/are primarily a non-cellulosic material such as polyester or polyester blend, and in one embodiment is/are a non-polymeric non-cellulosic material, e.g., natural fiber materials. The composition contains a source contact sheet including a staining reagent and a sink contact sheet, where the staining reagent interacts, associates, and/or binds with a biopolymer. The inventive method stains biopolymers using an electric field employing these source and sink contact sheets. In embodiments, the compositions are highly absorbent, liquid retaining, and fluid permeable, which maximize contact with the matrix by providing at least one of a smooth surface, uniform consistency, and pliability for improved conformation with the matrix surface. Without being held to a single theory, maximization of the contact between the disclosed compositions and the matrix provides uniform transfer of current by the electric field and results in improved staining and destaining.

U.S. Patent Application Publication No. 2010/0326828 discloses a composition and method for staining biopolymers after gel electrophoresis that uses paper materials, specifically blotting paper. A staining solution, including a stain such as Coomassie Blue R-250 or G-250, is either pre-absorbed or applied to a porous material such as the blotting paper. The solution-containing blotting paper is positioned to contact one side of an electrophoresis gel, and a second blotting paper, lacking the stain, is positioned to contact the other side of the gel forming an assembly. This assembly is arranged between a pair of electrodes and a DC voltage is applied to the electrodes and across the assembly. The voltage difference between the electrodes causes the stain to migrate out of the solution-containing blotting paper and into the gel, where the stain binds to biopolymers in the gel matrix. The voltage difference is maintained to cause any unbound stain to migrate completely through the gel and into the second blotting paper, destaining the gel matrix but not destaining the biopolymers in the matrix. The composition and method replace passive, diffusion-driven processes for staining electrophoretic separations; these may require several hours to complete, while the active electrically-driven staining process requires as short a time as six minutes.

As stated, the '828 application uses paper materials such as filter paper, blotting paper, paper pads, etc. that are cellulosic products. The commercially available eStain® 2.0 Protein Staining System (GenScript USA, Inc., Piscataway N.J.) is based on a cotton cellulose fiber paper.

The use of these cellulosic materials in the electrically-driven staining method yields exhibit undesirable effects, such as high backgrounds and/or blotchy backgrounds in electrophoresis gels. Without being limited to a specific theory, such undesirable backgrounds result from the non-uniform and relatively rigid surfaces of the paper materials that do not provide a substantially maximal and/or uniform contact with the matrix surface. Although the method disclosed in the '828 application has increased speed, its resultant high background forces a trade-off between staining time and low background levels, similar to diffusion-driven processes, which are often performed overnight to essentially completely remove background and improve the precision and/or accuracy of automated fingerprint detection methods and quantitation methods.

The disclosed compositions and methods use the reduced staining time achieved with electrically-driven staining method, as well as also providing substantially improved stain backgrounds that are both low and uniform. The disclosed compositions and methods are useful for and are used in, e.g., semi-automated or fully-automated electrophoretic separation processes used in electrophoretic fingerprint detection methods and quantitation methods.

One embodiment is an electrophoretic stain composition including a source sheet, which includes embodiments where the source sheet is a plurality of sheets, containing a stain solution, i.e., a stain dissolved in a suitable solvent, and a sink sheet or sheets containing a suitable solution, such as a destain solution. The sheet or sheets are generally planar, fluid-permeable contact sheet primarily of a non-cellulosic material or a cellulosic blend. The stain solution and/or destain solution may be sorbed to the fluid-permeable contact sheet, or may be sorbed to a reservoir layer contactable with a non-matrix contact side of the contact sheet. In one construction, the source sheet or sheets is a source electrophoretic stain composition including a stain. In another construction, the sink sheet or sheets is a sink electrophoretic stain composition including a destain solution.

One embodiment is an electrophoretic stain kit. The kit includes a first composition of an acid, an organic solvent, a staining reagent, i.e., a stain, and a first generally planar, fluid-permeable contact sheet primarily of a non-cellulosic material. Any one or more of the acid, organic solvent, and stain may be sorbed to the fluid-permeable contact sheet, or may be sorbed to a reservoir layer contacting a non-matrix contact side of the first contact sheet. The kit also includes a second composition of a suitable solution, such as a destain solution, and a second generally planar, fluid-permeable contact sheet primarily of a non-cellulosic material. A sorbent may be a non-primary component of the second gel contact sheet, or may be a sorbent layer contacting a non-matrix contact side of the second contact sheet.

One embodiment is a method of staining a matrix such as an electrophoretic gel containing a biopolymer. The method includes (a) preparing or constructing an assembly of (i) an electrophoretic gel containing the biopolymer (ii) a first generally planar, fluid-permeable contact sheet primarily of a non-cellulosic material having a matrix contact side in direct contact with a side of the electrophoretic gel and (iii) a second generally planar, fluid-permeable contact sheet primarily of a non-cellulosic material having a matrix contact side in direct contact with an opposite side of the electrophoretic gel; (b) positioning the assembly between a first electrode and a second electrode and in electrical contact with the electrodes; and (c) applying a DC current to the electrodes and across the assembly. Before applying the current, the first contact sheet is provided with a staining solution, and the second contact sheet is provided with at least a suitable solution, such as a destain solution.

In each embodiment, the generally planar, fluid-permeable contact sheets consist primarily of a non-cellulosic material, but are not necessarily cellulose-free. For example, the gel contact sheets may be manufactured from polyester or a polyester cellulose blend, with the sheet being principally polyester but including a lesser fraction of cellulose, e.g., non-woven cellulose fiber.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1D:
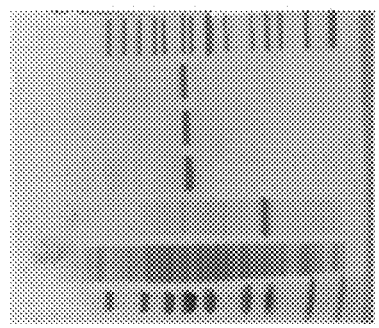
FIGS. 1A, B, C, D are pictures of electrophoresis gels processed with eStain® 2.0 Protein Staining System using the supplied blotting paper as a gel-contacting stain solution carrier and destaining sink contact sheet (FIGS. 1A, 1B), and gels stained using a conventional Coomassie staining protocol (FIGS. 1C, 1D).

A biopolymer includes, but is not limited to, a peptide, protein, RNA, DNA, single-stranded oligonucleotide, double-stranded oligonucleotide, oligosaccharide and any complexes, modifications, derivatives, etc. thereof. Examples of complexes include, but are not limited to, polypeptide-polypeptide complexes, RNA-polypeptide complexes, DNA-polypeptide complexes, polynucleotide-polynucleotide complexes, etc.

A matrix material includes any material in which a biopolymer is associated with, impregnated within, bound to, absorbed to, the matrix. In one embodiment, the matrix is configured for use in an electric field, typically a gel, e.g., SDS-polyacrylamide gel or native gel, but also including a membrane, filter, etc. used in known electrophoresis processes. In one embodiment, the biopolymer is contained within cells and/or tissue that are present on or associated with the matrix, such as a porous substrate, e.g., porous filter paper. In embodiments, the cells are fixed using methods known in the art, and the tissue is tissue sections that may be fixed and prepared according to methods known in the art.

The term sorbed includes adsorption, absorption, and the retention of fluids between fibers, or within the porosity of or in hollow fibers, due to surface tension and related forces.

In one embodiment, the composition for staining or otherwise tagging biopolymers in the matrix comprises a staining reagent, an acid, an organic solvent, a staining agent, and at least one generally planar contact sheet. In embodiments, the composition for staining may contain additives such as salts, chelating agents e.g., ethylene diamine tetraacetic acid (EDTA), fixatives, etc. In contrast to the porous, typically paper materials known in the art, the disclosed contact sheet is a fluid-permeable sheet primarily of a non-cellulosic material which exhibits a substantially uniform, e.g., non-porous, surface in contact with the matrix. In one embodiment, the sheet may consist primarily of polyester, and may be in the form of woven polyester fiber, or non-woven polyester fiber. In one embodiment, the sheet may consist primarily of polyester, but may also comprise a polyester cellulose blend. For example, the sheet or sheets may be in the form of a woven or non-woven polyester fiber and cotton cellulose fiber blend and/or felt. In embodiments, the sheet or sheets may be primarily polyacrylamide, polysaccharide, and/or agarose. In embodiments, the sheet or sheets may be primarily as described but include a mixture or blend with cellulose, alumina, silica, etc.

Specific examples of materials that can be used in the disclosed composition include woven polyester as in Contec Quiltec I wipes, non-woven polyester as in Contec SAT wipes or LymTech Scientific C3SH wipes, non-woven polyester cellulose as in LymTech Scientific C30 Poly/Cellulose wipes, polyester cellulose, non-woven polyester cellulose as in Contec Amplitude Ecotech wipes, non-woven polypropylene as in LymTech Scientific 7408 Compo wipe including thermally bonded inner cellulose layer, polypropylene and polypropylene blends, such as a multi-layered sheet having layers of polypropylene and inner layers of cellulose, and polyacrylamide such as Pierce Precise Tris-Glycine gels.

The acid may be an organic acid, e.g., acetic acid, citric acid, sulfosalicylic acid, phosphoric acid, hydrochloric acid, sulfuric acid, etc., and may be at a concentration in the range of about 0.1% v/v to about 20% v/v. In general, the acid may be any acid or mixture of acids known for use in electrophoretic separations, and is used to fix biopolymers within an electrophoresis gel during execution of the staining method. In one embodiment, the liquid phase of the composition includes five percent (5%) acetic acid.

The organic solvent may be a water soluble solvent, e.g., ethanol, methanol, isopropanol, etc., and may be a concentration in the range of about 1% v/v to about 50% v/v. In general, the organic solvent may be any solvent or mixture of solvents suitable for use with the electrophoretic separation target(s) and a selected stain. In one embodiment, the liquid phase of the composition includes 25% v/v ethanol. In one embodiment, the liquid phase of the composition includes 25% v/v isopropanol.

Optionally, the composition may include a buffering agent, such as sodium phosphate, Tris, MES, MOPS, etc., and may be at a concentration in the range of about 0.1% to about 10%, and at a pH of about pH 2 to about pH 11. In one embodiment, the liquid phase of the composition includes sodium phosphate buffer.

In one embodiment, the composition is a source composition including a staining reagent, i.e., a stain. In one embodiment, the stain is a protein stain, e.g., known protein stains including Coomassie Blue R-250 or Coomassie Blue G-250, at a concentration range of about 0.01% w/v to about 5% w/v. Other hydrophobic or charged stains including chromogenic, fluorescent, chemiluminescent, or bioluminescent molecules may be used, including stains for detecting protein modifications such as phosphorylation, glycosylation, acetylation, nitrosylation, SUMOylation, epitope tags, silver stains, and metal-protein complex stains. Other staining reagents used to tag biopolymers for other means of detection, such as non-protein biopolymers, include antibodies, nucleic acids, Fabs, scFv antibodies, aptamers, dendrimers, quantum dots, SYBR Green, SYTO 61, TOTO-3, ethidium bromide, propidium iodide, Hoechst, DAPI, etc. may be used. In one embodiment, the liquid phase of the composition includes or will include as subsequently described 0.01% w/v of Coomassie Blue R-250.

In one embodiment, the acid, organic solvent, and staining reagent are sorbed to the fluid-permeable contact sheet. The composition may be packaged in a fluid-impermeable bag (e.g., a plastic food storage bag with a secure seal), sachet, overwrap, etc. that is removed prior to application of the composition to a gel. In one embodiment, the composition may further include a reservoir layer contactable with a non-matrix contact side of the contact sheet. The reservoir layer may comprise a sorbent material, such as cellulose, that may hold a substantial fraction of the acid, staining reagent, organic solvent, optional buffer, etc. for fluid communication through the contact sheet to the matrix. In one embodiment, the staining solution or a component may be dried onto the contact sheet and rehydrated before use.

In one embodiment, the composition is a sink composition including a solution, such as a destaining solution. In one embodiment, the destain solution comprises an organic solvent, an acid, water, and optionally comprises a buffering agent. In one embodiment, the sink composition is paper. In one embodiment, the sink composition is the same sheet material as the staining sheet but contains different described solutions. In one embodiment, the sink composition may further contain a sorbent, such as cellulose, although at a lesser fraction than the non- or partially-cellulosic material that is incorporated into the contact sheet. In one embodiment, the sink composition may further contain a sorbent such as alumina and silica. In one embodiment, the sink composition may further include the destain solution and/or sorbent as a layer in contact with a non-matrix contact side of the sink contact sheet. The sorbent may preferentially sorb the staining reagent. For example, where the staining reagent is Coomassie Blue R-250, Coomassie Blue G-250, or a similar charged molecule, the sorbent may include ion exchange cellulose that preferentially binds organic anions.

As is apparent from the first and second constructions, the composition need not omit all cellulosic materials, but instead provides a principally non- or partially-cellulosic material layer that is deposited in direct contact with the surface of the matrix, e.g., electrophoresis gel. By replacing the cellulosic materials with essentially a non- or partially-cellulosic sheet, increased staining/destaining speed was retained while the stain background and blotchiness of an electrophoretically destained gel was dramatically decreased.

Figure 6:
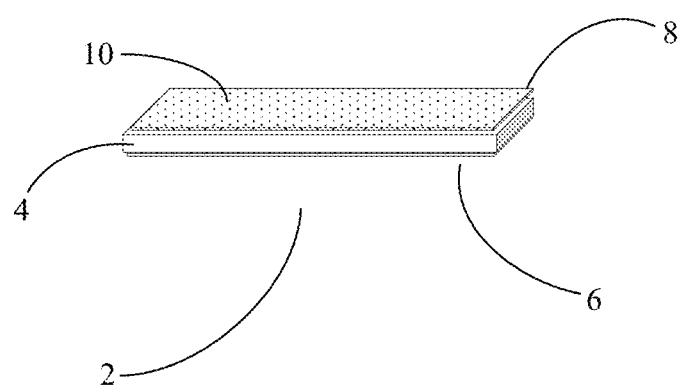
FIG. 6 depicts a kit according to the present disclosure that includes a matrix, a first matrix contact sheet, and a second matrix contact sheet, wherein a destain solution is absorbed into the second matrix contact sheet.

One embodiment is a kit containing a first composition including an acid, an organic solvent, a staining reagent, and a first generally planar, fluid-permeable contact sheet(s) consisting primarily of a non-cellulosic material. Any one or more of the acid, organic solvent, and staining reagent may be sorbed to the fluid-permeable contact sheet, may be sorbed to a reservoir layer contactable with non-gel contact side of the first contact sheet, or may be provided separately. In one embodiment, the kit further comprises a second composition including an acid, an organic solvent, a sorbent, and a generally planar, fluid-permeable contact sheet consisting primarily of a non-cellulosic material. The sorbent may be a non-primary component of the contact sheet, or may be a sorbent layer contacting a non-gel contact side of the contact sheet. The acid, organic solvent, and non-cellulosic material of the respective compositions need not be the same. The sorbent may preferentially sorb the particular staining reagent of the first composition of the kit. The kit may also include instructions for staining a biopolymer in a matrix that is contacted by the fluid-permeable contact sheet(s). FIG. 6 depicts contents of an exemplary kit 2 that includes a matrix 4, a first contact sheet 6, and a second contact sheet 8. A destain solution 10 is absorbed into the second contact sheet 8.

One embodiment is a method of staining a matrix using an electric field, such as an electrophoretic matrix, such as a gel, containing biopolymers. After electrophoresis, the matrix with the separated biopolymers can be stained using pre-assembled non-cellulosic sheets adsorbed with a staining solution (first composition; cathode sheets) and destaining solution (second composition; anode sheets), or it can be stained with non-cellulosic sheets adsorbed with a staining solution (first composition; cathode sheets) and destaining solution (second composition; anode sheets) pre-adsorbed by the user.

In one embodiment, after electrophoresis, the gel was removed from the electrophoresis cassette and pre-assembled solution-bearing sheets were removed from their packing and positioned on the appropriate sides of the electrophoresis gel with previously separated biopolymers. A DC voltage was applied across the sheets-gel-sheets assembly for seven minutes using Pierce Fast G2 Blotter (25 Volts, 1.0-1.3 Amp (constant)) or eStain 2.0 Protein Staining System.

In one embodiment, a user places the non-cellulosic sheets into separate containers and adds 13-15 ml staining solution (first composition) and 13-15 ml destaining solution (second composition) ensuring that the solutions are evenly adsorbed into the sheets. After electrophoresis, the gel and pre-made solution-bearing sheets are positioned on the appropriate sides of an electrophoresis gel with previously separated biopolymers. A DC voltage is applied across the sheets-gel-sheets assembly for seven minutes using Pierce Fast G2 Blotter (Thermo Scientific) (25 Volts, 1.0-1.3 Amp (constant)) or eStain 2.0 Protein Staining System.

EXAMPLE 1

Figure 1C:
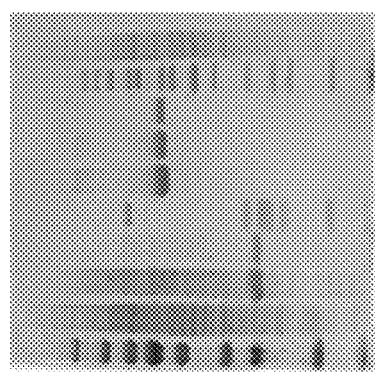
Figure 1B:
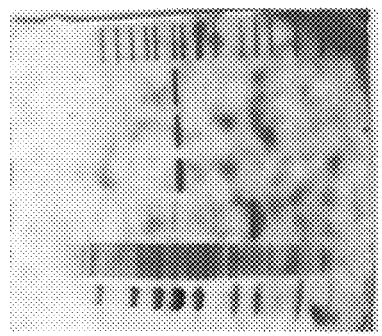
Figure 1A:
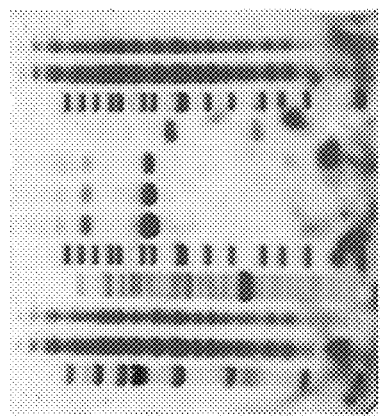

FIGS. 1A-D show a comparison of SDS-PAGE gels stained electrophoretically using filter paper and by conventional Coomassie staining protocol. Cell lysates, purified proteins, and molecular weight ladders were loaded and separated by electrophoresis on polyacrylamide gels (FIG. 1A: 4%-12% NuPage Bis Tris; FIGS. 1B, D: 4%-20% Criterion Tris-HCl; FIG. 1C: 4%-20% Midi Tris-Glycine) according to the gel suppliers' recommendations. After electrophoresis, the midi gels were cut in half and mini gel was left as is. FIGS. 1A and B gels were stained using eStain Protein Staining Pad R-250 (GenScript L02011) which uses filter paper for seven minutes according to the manufacturer's instructions. FIGS. 1 C and D gels were stained with Imperial Protein Stain (Thermo Scientific product #24615) by first washing the gel three times ten minutes with ultra-pure water and staining for 60 minutes in the stain. The gel was destained overnight in water. These results showed the uneven and splotchy staining artifacts produced during electrophoretic staining using conventional filter paper compared to the even staining produced by Coomassie staining.

EXAMPLE 2

Figure 2A:
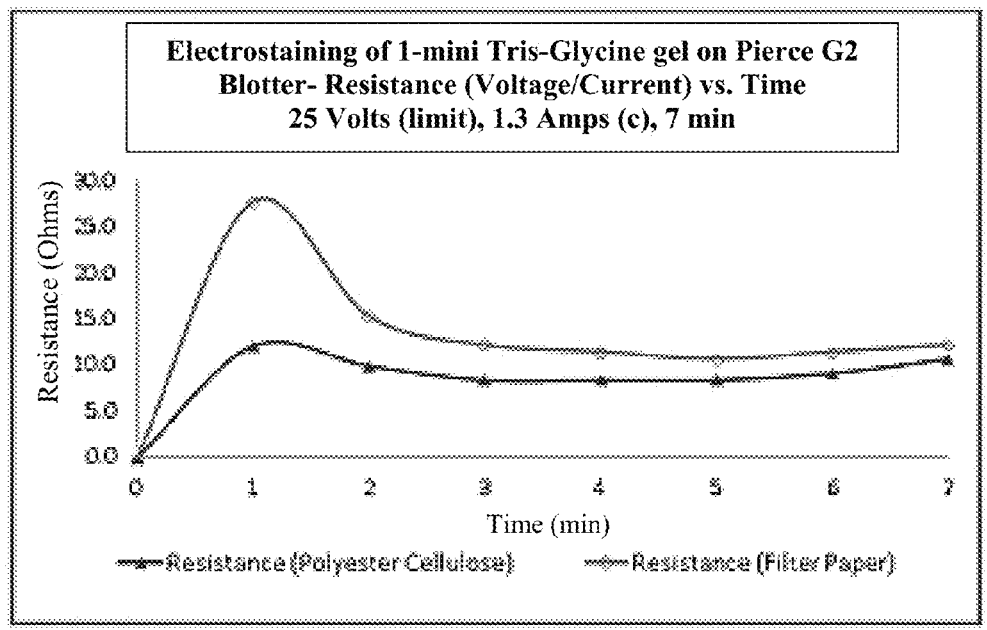
FIGS. 2A-B compare electrical resistance (FIG. 2A) and temperature generated (FIG. 2B) during the electrophoretic staining procedure using filter paper or polyester cellulose material as a gel-contacting stain solution carrier and destain sink contact sheet.
Figure 2B:
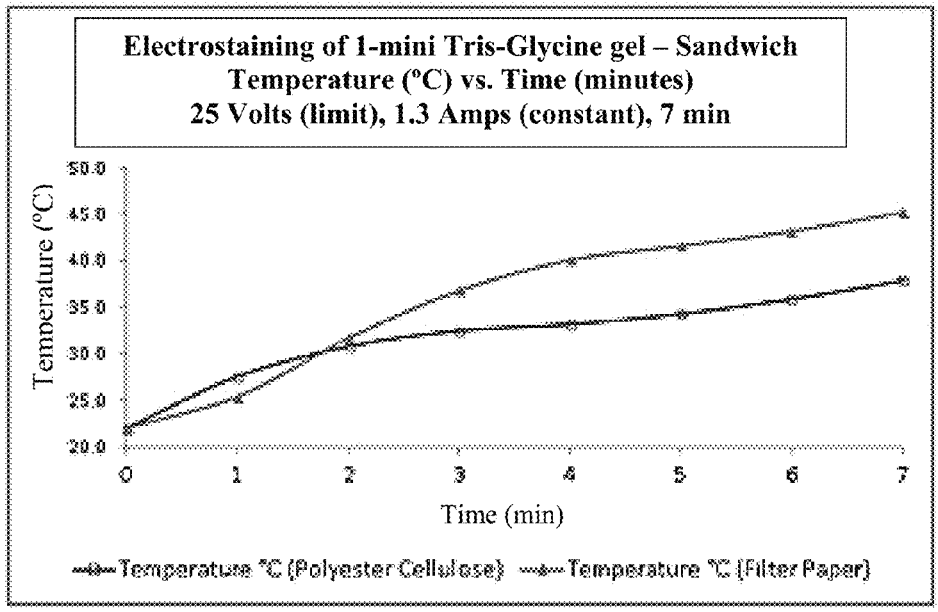

FIGS. 2A, B show comparison of the resistance (FIG. 2A) and temperature generated (FIG. 2B) during the electrophoretic staining procedure. Biomolecules were separated on polyacrylamide gels as in FIG. 1 and then prepared for electrophoretic staining by placing the gels between a staining pad of either polyester cellulose sheets or conventional filter paper. The anode solution was 30% ethanol, 5% acetic acid and the cathode solution was 30% ethanol, 5% acetic acid, 0.01% Coomassie R-250. A DC voltage applied across the sheets-gel-sheets assembly for seven minutes using Pierce Fast G2 Blotter (25 Volts, 1.0-1.3 Amp (constant)). The resistance and temperature were measured and plotted. These results demonstrated lower resistance and heat generation during electrostaining using polyester/cellulose material compared to filter paper.

EXAMPLE 3

Figure 3B:
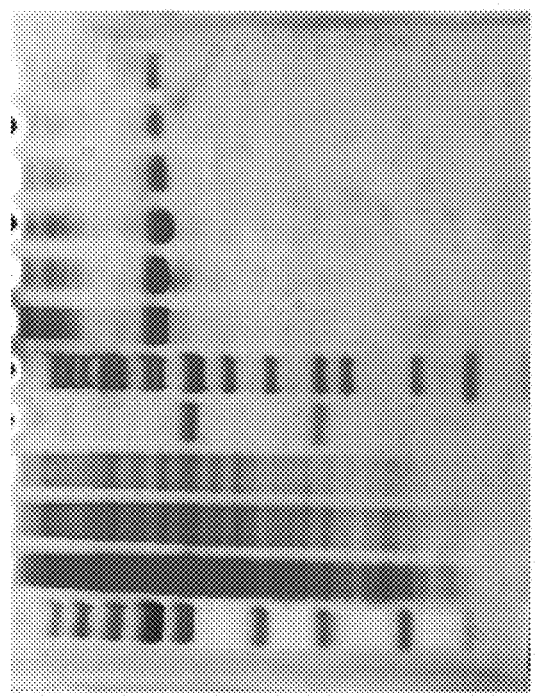
FIGS. 3A-B are pictures of electrophoresis gels processed using the procedure of U.S. Patent Application Publication No. 2010/0326828 on the GenScript eStain 2.0 Protein Staining System using a blotting pad as a gel-contacting stain solution carrier and destaining sink contact sheet (FIG. 3A), compared to using polyester cellulose material (FIG. 3B).
Figure 3A:
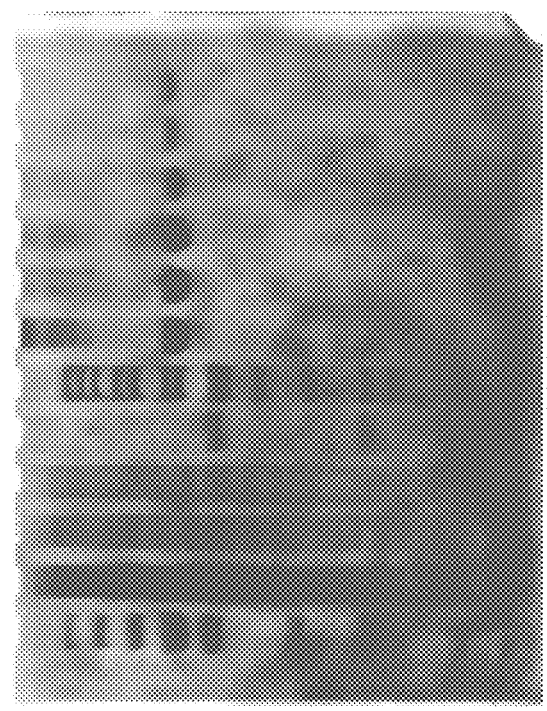

FIGS. 3A, B show improved staining and destaining of polyacrylamide gels when electrostaining was performed using polyester cellulose material in the staining and destaining pads compared to conventional filter paper. Protein samples were separated by electrophoresis on 4%-20% Precise Tris-Glycine polyacrylamide gels. After electrophoresis, both gels were electrostained using eStain 2.0 Protein Staining System. Cellulose filter paper (FIG. 3A) or polyester cellulose material (LymTech C30L; 7 layers) (FIG. 3B) were soaked in cathode-staining solution (25% ethanol, 5% acetic acid, 0.01% Coomassie R-250) and anode-destaining solution (25% ethanol, 5% acetic acid) and placed on either side of the unstained gel. The assembled sandwiches were placed into eStain Protein Staining System and the gels were electrostained for seven minutes. The photograph represents results from the inventive method showing less blotchy staining and more even staining across the gel. In comparison to FIGS. 1 and 3A, FIG. 3B shows a lighter stain background of the processed electrophoresis gel and lacking the significant blotching artifacts that appear in FIGS. 1A and B particularly in the lower quadrant, and in FIG. 3A particularly in the lower center area. There was thus significant improvement in destaining efficiency without resort to the passive, diffusion-driven staining and destaining processes typically used to obtain complete removal of stain background just by using supple material, e.g., material that easily conforms to the given surface, instead of more rigid filter paper.

EXAMPLE 4

Figure 4C:
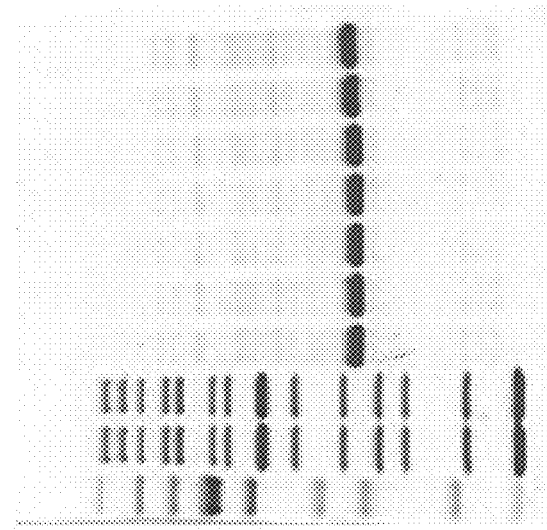
FIGS. 4A, B, C are pictures of electrophoresis gels processed using the procedure of U.S. Patent Application Publication No. 2010/0326828 on the G2 Fast Blotting instrument using a blotting pad as a gel-contacting stain solution carrier and destaining sink contact sheet (FIG. 4A) compared to using polyester cellulose material (FIG. 4B, 4C).
Figure 4B:
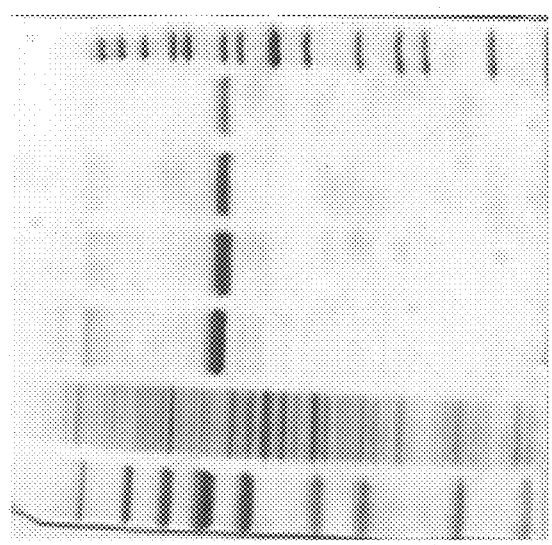
Figure 4A:
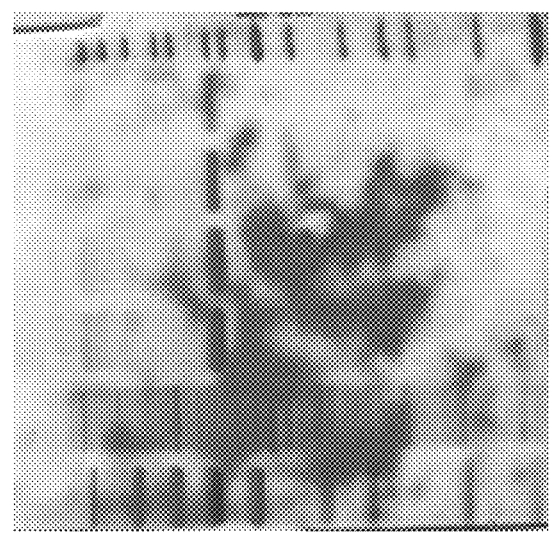

FIGS. 4A-C show improved staining and destaining of polyacrylamide gels with electrostaining using polyester cellulose compared to filter paper using Thermo Scientific G2 Fast Blotter instrument. Protein samples were separated by electrophoresis on 4%-20% Criterion HCl (FIGS. 4A, 4B) polyacrylamide gel and 4%-20% Midi Tris-Glycine polyacrylamide gel (FIG. 4C). After electrophoresis, both midi gels were cut in half and electrostained using Pierce Fast G2 Blotter instrument. Cellulose filter paper (FIG. 4A) or polyester cellulose material (LymTech C30L; 7 layers) (FIG. 4B, 4C) were soaked in cathode staining solution (25% ethanol, 5% acetic acid, 0.01% Coomassie R-250) and anode destaining solution (25% ethanol, 5% acetic acid) and placed on either side of the unstained gel. The assembled sandwiches were electrostained using Pierce Fast G2 Blotter for seven minutes at 1.3 Amps (constant) and 25 Volts (limit).

EXAMPLE 5

Figures 5A, 5B, 5C, 5D:
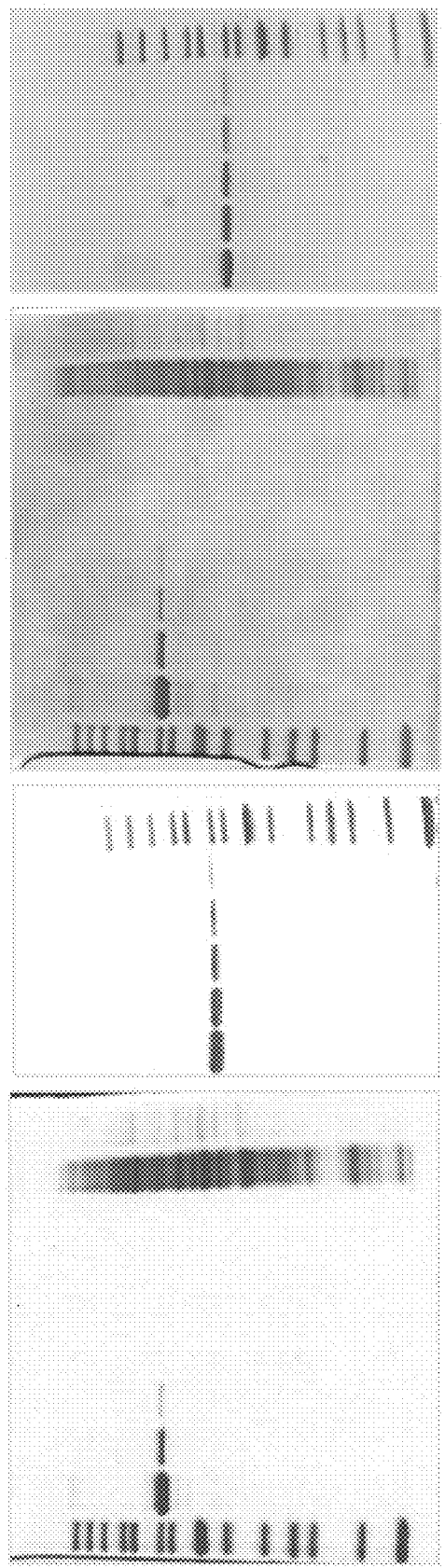
FIGS. 5A, B, C, D are pictures of electrophoresis gels stained using commercially available Coomassie stain according to conventional methods (FIGS. 5C, 5D), compared to gels electrostained using polyester cellulose as the staining and destaining pads (FIGS. 5A, 5B) performed on the G2 Fast Blotting instrument.

FIGS. 5A-D show the superior performance of electrophoretic staining using polyester cellulose compared to conventional Coomassie staining. PageRuler Unstained Protein Ladder and/or HeLa lysate was loaded onto 4%-20% Midi Tris-Glycine gel (FIG. 5A, 5C) and 4-20% Criterion HCl gel (FIGS. 5B, 5D) together with bovine serum albumin (BSA) that was serially diluted and prepared for SDS-PAGE. The gels were subjected to electrophoresis according to the gel suppliers' recommendations. After electrophoresis, the midi-sized gels were cut in half. Gel A was electrostained using Pierce Fast G2 Blotter where a polyester cellulose material (LymTech C30L; 7 layers) soaked with an anode solution (30% isopropanol, 5% acetic acid) was placed on the anode plate, followed by the unstained gel and a polyester cellulose material (LymTech C30L; 7 layers) soaked with a cathode solution (30% isopropanol, 5% acetic acid, 0.01% Coomassie R-250). Gel B was electrostained using Pierce Fast G2 Blotter using a polyester cellulose material (LymTech C30L; 7 layers) soaked with an anode solution (35% ethanol, 5% acetic acid) was placed on the anode plate, followed by the unstained gel and a polyester cellulose material (LymTech C30L; 7 layers) soaked with a cathode solution (35% ethanol, 5% acetic acid, 0.01% Coomassie R-250). The cathode plate was placed on the top of the stacks and the cassettes were inserted into the Pierce G2 Fast Blotter Control Unit for seven minutes with constant amperage (1.3 Amps) and limited voltage (25 Volts). FIG. 5C and FIG. 5D gels were stained with Imperial Protein Stain by first washing the gels three times fifteen minutes with ultra-pure water and staining for sixty minutes in the stain. The gels were destained overnight in water.

For comparison with conventional staining, the gel was conventionally stained using commercially available pre-formulated Coomassie stain, e.g., Pierce Imperial Protein Stain (FIGS. 1 and 5). After electrophoresis the gel was removed from the cassette, washed three times for 10-15 minutes each with gentle agitation with ultra-pure water, and then stained for sixty minutes with gentle agitation. The staining solution was decanted and the gel was washed three times for twenty minutes each in water or overnight with gentle agitation.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

What is claimed is:

1. A kit for electrophoretically staining a biopolymer in a matrix comprising
    a first non-cellulosic or modified cellulosic matrix contact sheet contacting a first side of the matrix,
    a second matrix contact sheet contacting a second side of the matrix and comprising a non-cellulosic or partially cellulosic material,
    a stain solution comprising a stain reagent and a solvent, the stain solution optionally being absorbed within the first matrix contact sheet, and
a destain solution comprising an organic solvent, an acid, water, and optionally a buffering agent, the destain solution being absorbed within the second matrix contact sheet.

2. The kit of claim 1 where the stain solution is provided absorbed into the first matrix contact sheet.

3. The kit of claim 1 where the stain solution comprises 25% ethanol, 5% acetic acid, and 0.01% Coomassie Brilliant Blue dye R-250 or G-250, and the destain solution comprises 25% ethanol and 5% acetic acid.

4. The kit of claim 1 further comprising instructions for staining the biopolymer in the matrix using an electric field.

5. The kit of claim 1 where the first matrix contact sheet further comprises at least one additional sheet distal from the first side of the matrix and/or the second matrix contact sheet further comprises at least one additional sheet distal from the second side of the matrix, the at least one additional sheet being the same or different from the first matrix contact sheet and/or the second matrix contact sheet.

6. The kit of claim 1 where the first matrix contact sheet is capable of absorbing at least 5 ml of the stain solution, but less than 15 ml of the stain solution; a thickness of the first matrix contact sheet is less than 0.5 inches; and/or the matrix contact surface is sufficient to provide maximum contact between the first matrix contact sheet and the matrix.

7. The kit of claim 1 where the first matrix contact sheet or the first and the second matrix contact sheet is polyester, polyester/cellulose blend, polypropylene, polypropylene/cellulose blend, polyacrylamide, nitrocellulose, non-cellulose, polysaccharide, agarose, felt, polyvinylidene fluoride (PVDF), polyvinylidene difluoride, fine woven cotton, wool, regenerated cellulose fiber, Lyocell, and combinations thereof.

8. The kit of claim 7 where the first matrix contact sheet is polyester, polyester/cellulose blend, polypropylene, polypropylene/cellulose blend, polyacrylamide, nitrocellulose, non-cellulose, polysaccharide, agarose, felt, polyvinylidene fluoride (PVDF), polyvinylidene difluoride, regenerated cellulose fiber, Lyocell, and combinations thereof.

9. The kit of claim 5 where the at least one additional sheet is polyester, polyester/cellulose blend, polyacrylamide, nitrocellulose, polysaccharide, agarose, felt, polyvinylidene fluoride (PVDF), polyvinylidene difluoride, a fabric, a foam, a sponge, and combinations thereof.

10. The kit of claim 5 where the stain solution is present in the at least one additional sheet which is not in contact with the matrix.

11. The kit of claim 1 where the second matrix contact sheet comprises a sorbent selected from the group consisting of wound dressing non-adhesive material, woven and non-woven cotton, foam, felt, agarose, agarose/polyacrylamide matrix, alumina, silica, polysaccharides, polymer, and combinations thereof.

12. The kit of claim 1 where the stain solution comprises an acid, an organic solvent, and the stain reagent.

13. The kit of claim 12 where the acid is acetic acid and the organic solvent is ethanol or isopropanol.

14. The kit of claim 12 where the stain solution further comprises a buffering agent.

15. The kit of claim 14 where the buffering agent is sodium phosphate.

16. The kit of claim 1 where the stain reagent is a protein stain, and is selected from the group consisting of Coomassie Blue R-250, Coomassie Blue G-250, silver stain, hydrophobic or charged staining reagents, neutral staining reagents, and protein modification stains.

17. The kit of claim 16 where the charged staining reagents include chromogenic, fluorescent, chemiluminescent, and/or bioluminescent molecules.

18. The kit of claim 16 where the neutral staining reagent further comprises a non-charged organic or non-organic solvent.

19. The kit of claim 16 where the protein modification is at least one of phosphorylation, glycosylation, acetylation, nitrosylation, SUMOylation, or epitope tags.

20. The kit of claim 1 where the matrix is selected from the group consisting of SDS polyacrylamide gels, native polyacrylamide gels, membranes, and filters.

* * * * *